United States Patent
Covitch et al.

(10) Patent No.: US 10,362,970 B2
(45) Date of Patent: Jul. 30, 2019

(54) PHASE-TO-AMPLITUDE/SLOPE MAPPING

(71) Applicant: KONINKLIJKE PHILIPS N.V., Eindhoven (NL)

(72) Inventors: Adam Jacob Covitch, Cleveland, OH (US); Paul Klahr, Beachwood, OH (US)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 488 days.

(21) Appl. No.: 15/001,286

(22) Filed: Jan. 20, 2016

(65) Prior Publication Data
US 2016/0135718 A1   May 19, 2016

Related U.S. Application Data

(62) Division of application No. 13/700,161, filed as application No. PCT/IB2011/051840 on Apr. 27, 2011, now Pat. No. 9,265,452.
(Continued)

(51) Int. Cl.
*A61B 5/00* (2006.01)
*A61B 6/00* (2006.01)
(Continued)

(52) U.S. Cl.
CPC .............. *A61B 5/113* (2013.01); *A61B 6/527* (2013.01); *A61B 6/5288* (2013.01); *A61B 6/541* (2013.01);
(Continued)

(58) Field of Classification Search
CPC ..... A61B 5/113; A61B 5/7285; A61B 6/5288; A61B 6/541
See application file for complete search history.

(56) References Cited

U.S. PATENT DOCUMENTS 4,122,454 A   10/1978 Frosch
4,727,882 A   3/1988 Schneider
(Continued)

FOREIGN PATENT DOCUMENTS

WO   WO2008/029121 A1 *   3/2008
WO   2010066265   6/2010

OTHER PUBLICATIONS

Rietzel et al., Improving retrospective sorting of 4D computed tomography data, Med. Phys. 33 (2) Feb. 2006.*
(Continued)

*Primary Examiner* — Michael J Dalbo
(74) *Attorney, Agent, or Firm* — Larry Liberchuk

(57) ABSTRACT

A method includes obtaining a signal that includes a plurality of cycles and generating a map that maps motion phases to the signal based on both an amplitude and a slope of the signal. A system includes a processor that identifies a set of motion signal timestamps, for a plurality of motion cycles in a motion signal indicative of cyclic motion of a moving object, based on a predetermined motion phase of interest and a phase-to-amplitude/slope mapping, wherein the set of motion signal timestamps correspond to a common signal amplitude. A method include identifying a peak of a plurality of peaks in a motion cycle of a noisy cyclic signal having irregular periodicity, wherein the peak corresponds to a point lying between two points with amplitudes below a predetermined threshold, comparing points before and after the peak with the peak, and identifying the peak as a local maximum when the peak is greater than the points.

14 Claims, 7 Drawing Sheets

Related U.S. Application Data

(60) Provisional application No. 61/351,310, filed on Jun. 4, 2010.

(51) Int. Cl.
  *G06K 9/00* (2006.01)
  *A61B 5/113* (2006.01)
  *G06F 17/00* (2019.01)

(52) U.S. Cl.
  CPC ........... *G06F 17/00* (2013.01); *G06K 9/0053* (2013.01); *A61B 5/7285* (2013.01)

(56) References Cited

U.S. PATENT DOCUMENTS

| | | | |
|---|---|---|---|
| 4,777,648 A | 10/1988 | Gardner | |
| 4,967,751 A | 11/1990 | Sterzer | |
| 5,315,512 A | 5/1994 | Roth | |
| 5,482,042 A * | 1/1996 | Fujita | A61B 5/1077 600/428 |
| 6,135,952 A | 10/2000 | Coetzee | |
| 6,658,276 B2 | 12/2003 | Kianl | |
| 7,443,946 B2 | 10/2008 | Deller | |
| 7,574,249 B2 | 8/2009 | Piacsek | |
| 8,672,847 B2 | 3/2014 | Miyachi | |
| 8,699,772 B2 | 4/2014 | Allmendinger | |
| 9,265,452 B2 * | 2/2016 | Covitch | A61B 5/113 |
| 2002/0161291 A1 | 10/2002 | Kianl | |
| 2004/0138557 A1 | 7/2004 | Le | |
| 2005/0201509 A1 | 9/2005 | Mostafavi | |
| 2005/0249667 A1 | 11/2005 | Tuszynski | |
| 2006/0074300 A1 | 4/2006 | Green | |
| 2007/0154035 A1 | 7/2007 | Fukui | |
| 2007/0172029 A1 | 7/2007 | Felmlee | |
| 2007/0237289 A1 * | 10/2007 | Deller | A61B 6/541 378/8 |
| 2009/0110238 A1 * | 4/2009 | Li | A61B 6/541 382/103 |
| 2010/0152600 A1 * | 6/2010 | Droitcour | A61B 5/05 600/534 |
| 2011/0075906 A1 | 3/2011 | Allmendinger | |
| 2012/0116229 A1 | 5/2012 | Miyachi | |

OTHER PUBLICATIONS

Fitzpatrick, et al., "Displacement-based binning of time-dependent computed tomography image data sets"; 2006; Med. Phys.; 33(1)235-246.

Langner, et al., "Accuracy in the localization of thoracic and abdominal tumors using respiratory displacement velocity and phase"; 2009; Med. Phys., 36(2)386-393.

Pan, et al., "Improvement of the cine-CT based 4D-CT imaging", 2007; Med. Phys.; 34(11)4499-4503.

Rietzel, et al., "Improving retrospective sorting of 4D computed tomography data", 2006; Med Phys.; 33(2)377-379.

Wink, et al., "Phase versus amplitude sorting of 4d-CT data"; 2006; Journal of Applied Medical Physics; 7(1)77-85.

* cited by examiner

PHASE-TO-AMPLITUDE/SLOPE MAPPING

CROSS REFERENCE TO RELATED APPLICATIONS

This application is a Divisional application of U.S. patent application Ser. No. 13/700,161 filed Nov. 27, 2012, which is a national filing of PCT application Serial No. PCT/IB2011/051840 filed Apr. 27, 2011, published as WO 2011/151740 on Dec. 8, 2011, which claims the benefit of U.S. Provisional Application No. 61/351,310 filed Jun. 4, 2010, all of which are incorporated herein by reference.

DESCRIPTION

The following generally relates to phase-to-amplitude/slope mapping and is described herein with particular application to a cyclic signal having irregular periodicity; other applications are also contemplated herein.

In imaging, respiratory phase-based gating of a respiratory signal, which is concurrently obtained while scanning a patient, has been used to identify projection data corresponding to a particular respiratory phase of interest (e.g., full inspiration, full expiration, or somewhere in between) for procedures where a patient breathes freely rather than holding his/her breath. With this approach, the respiratory signal has been divided into individual breathing cycles (based on signal maxima and minima), and each cycle is divided into phases ranging from the beginning of the cycle (0%) (e.g., full inspiration or expiration or) to the end of the cycle (99%).

FIG. 1 shows an example of the above. In FIG. 1, the y-axis represents signal amplitude (i.e. the mechanical state of the lungs, including expansion and contraction) and the x-axis represents time. For this example, a breathing cycle 102 is defined to begin with full inspiration or lung expansion, which corresponds to the signal maximum 104 of the cycle 102. In this example, the 0% phase is assigned to the maximum 104. The remaining portion of the cycle 102 is linearly divided into a plurality of phases such as 25%, 50%, 75%, and 99% of the cycle 102, relative to the maxima 104.

For reconstruction, a set of timestamps for a particular phase of interest is identified, based on percentage of the cycle, and conveyed to the reconstructor, which uses the timestamp to identify projection data to reconstruct. By way of example, in FIG. 1, where the 75% phase is the phase of interest, the timestamp 112 for the cycle 102 is identified and conveyed to the reconstructor. For the other cycles in FIG. 1, the timestamps 112, 114, 116, 118, and 120 are identified as corresponding to the 75% phase and conveyed to the reconstructor.

Unfortunately, there are several problems with this assumption: (a) the rate of expiration is generally less than the rate of inspiration so the phases do not linearly span across a cycle; (b) the breathing cycle shape may be different cycle to cycle (as can be seen in FIG. 1); and (c) the mechanical state (amplitude) of the lungs during inhalation is not guaranteed to be the same during exhalation. For example, in FIG. 1, the timestamps corresponding to point 112, 116, and 120 are nearer to or at full expiration where the lungs are contracted and the amplitude is at a minimum, whereas the timestamps 114 and 118 correspond to mechanical states during inspiration where the lungs are partially expanded and have greater amplitude. As a consequence, the anatomy in the reconstructed image data may not align, which may introduce motion artifact into the reconstructed image data.

Aspects of the present application address the above-referenced matters and others.

According to one aspect, a method includes obtaining a signal that includes a plurality of cycles and generating a map that maps motion phases to the signal based on both an amplitude and a slope of the signal.

According to another aspect, a system includes a processor that identifies a set of motion signal timestamps, for a plurality of motion cycles in a motion signal indicative of cyclic motion of a moving object, based on a predetermined motion phase of interest and a phase-to-amplitude/slope mapping, wherein the set of motion signal timestamps correspond to a common signal amplitude.

According to another aspect, a method includes identifying a peak from a plurality of peaks in a motion cycle of a noisy cyclic signal having irregular periodicity, wherein the peak corresponds to a point lying between two points with amplitudes below a predetermined threshold, comparing points before and after the peak with the peak, and identifying the peak as a local maximum when the peak is greater than the surrounding points.

The invention may take form in various components and arrangements of components, and in various steps and arrangements of steps. The drawings are only for purposes of illustrating the preferred embodiments and are not to be construed as limiting the invention.

FIG. 2 illustrates an imaging system 200 such as a computed tomography (CT) scanner. However, in other embodiments, the imaging system 200 may include one or more other imaging modalities such as x-ray, Positron Emission Tomography (PET), Single Photon Emission Computed Tomography (SPECT), Magnetic Resonance Imaging (MRI), Ultrasound (US), and/or other imaging modalities.

Figure 1:
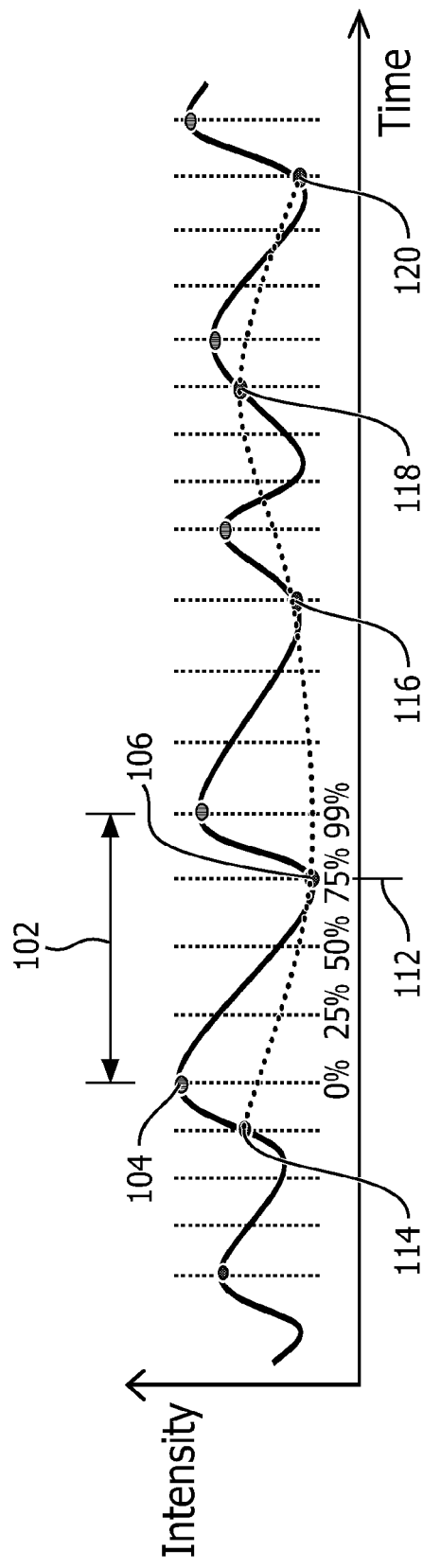
FIG. 1 illustrates prior art.

The imaging system 200 includes a stationary gantry 202 and a rotating gantry 204, which is supported by the stationary gantry 202. The rotating gantry 204 rotates around an examination region 206 about a longitudinal or z-axis.

A radiation source 208, such as an x-ray tube, is supported by the rotating gantry 204 and rotates with the rotating gantry 204, and emits radiation. A radiation sensitive detector array 210, located opposite the source 208 and across the examination region 206, detects radiation that traverses the examination region 206 and generates projection data corresponding to the detected radiation.

A support 212, such as a couch, supports the object or subject in the examination region 206. A motion monitor 214 monitors a motion state of a moving object during scanning and generates a motion signal indicative thereof. Examples of moving objects include, but are not limited to, the lung(s) or the heart of a patient, or other object with recurring regular or irregular cyclic motion.

A motion phase correlator 216 correlates motion phases with imaging or scan acquisition timestamps. As described in greater detail below, in one instance, this is achieved by correlating motion phases with the motion signal based on both an amplitude and a slope of the cycles in the motion signal. The resulting correlation can be used to identify timestamps of projection data, for different cycles, that corresponds to the same motion phase and that have a common or same mechanical amplitude or state. This may facilitate mitigating motion artifact due to misalignment of structure across the different cycles.

A reconstructor 218 reconstructs projection data and generates volumetric image data indicative of the examination region 206. The reconstructor 218 is configured to selectively reconstruct project data based on timestamps identified via the motion phase correlator 216 for a phase of interest. The reconstructor 218 may employ various reconstruction algorithms, and the projection data from a single or multiple acquisitions may be reconstructed to generate a single image.

A general purpose computing system serves as an operator console 220, which includes human readable output devices such as a display and/or printer and input devices such as a keyboard and/or mouse. Software resident on the console 220 allows the operator to control the operation of the system 200, for example, by allowing the operator to select a scanning protocol, initiate scanning, select a reconstruction algorithm (e.g., a motion gated reconstruction), etc.

It is to be appreciated that the motion phase correlator 216 may be part of the system 100, for example, part of the console 220 or otherwise, or remote from the system 100, for example, part of workstations, distributed across a network, and/or otherwise. Furthermore, the motion phase correlator 216 may be implemented by one or more processors processing computer readable instructions embedded or encoded on computer readable medium such as memory.

Figure 3:
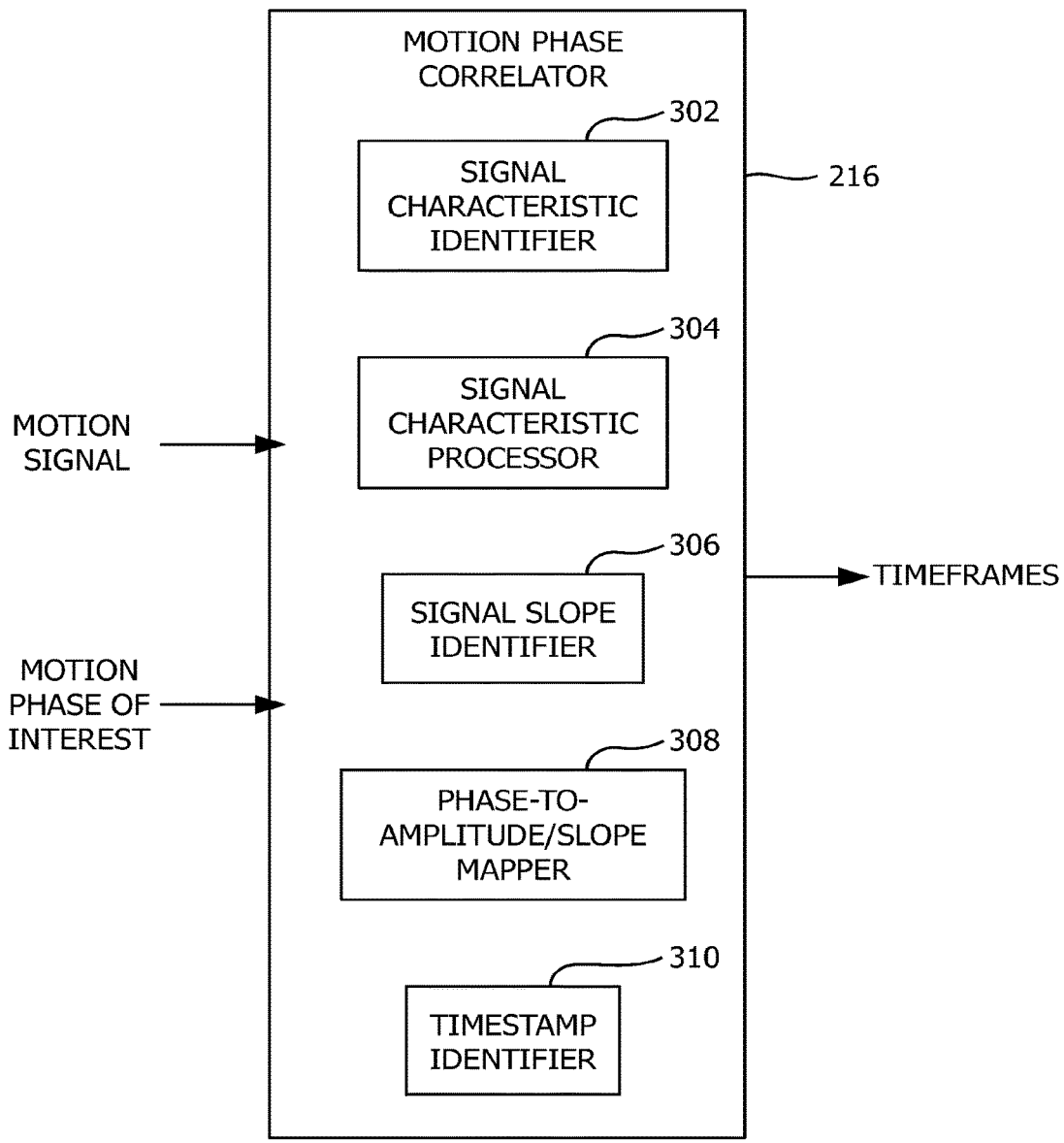
FIG. 3 illustrates example motion phase correlator.

FIG. 3 illustrates an example motion phase correlator 216.

A signal characteristic identifier 302 identifies one or more characteristics of a motion signal. This may include identifying one or more characteristics for one or more of the cycles of the motion signal. Examples of such characteristics include, but are not limited to, maxima and minima and/or other data points.

A signal characteristic processor 304 processes the identified signal characteristic(s). This may include determining one or more statistics (e.g., mean, median, maximum, minimum, etc.) and/or other information for the identified signal characteristic(s). In one instance, the statistic relates to the amplitude of the signal for one or more cycles.

A signal slope identifier 306 identifies descending and ascending regions in the cycles in the motion signal.

A phase-to-amplitude/slope mapper 308 maps motion phases to the motion signal based on the processed identified signal characteristic and the identified slopes.

A timestamp identifier 310 identifies timestamps in the motion signal that correspond to a motion phase of interest and have a similar signal amplitude based on the mapping.

The motion phase correlator 216 is now described in connection with processing a cyclic signal with irregular periodicity such as a respiratory signal obtained concurrently with imaging a subject. Other suitable signals include other cyclic signal including, but not limited to noisy cyclic signals with irregular periodicity.

Figure 4:
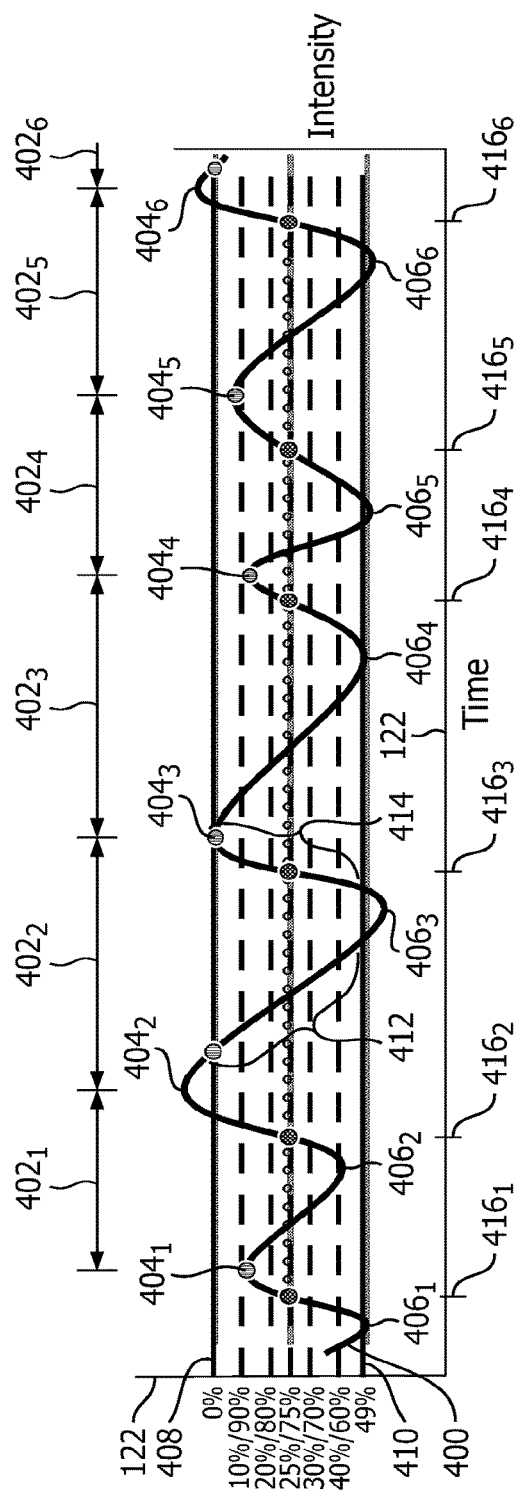
FIG. 4 illustrates an example approach for mapping motion phase to the amplitude and slope of a cycle in a motion signal.

Turning to FIG. 4, a signal 400 includes a plurality of breathing (inspiration and expiration) cycles $402_1$-$402_6$ having varying amplitudes and time widths. In FIG. 4, the y-axis represents signal amplitude (mechanical amplitude) and the x-axis represents time.

The signal characteristic identifier 302 identifies maxima $404_1$-$404_6$ and minima $406_1$-$406_6$ of the respiratory cycles $402_1$-$402_6$ of the respiratory signal 400. In this example, for a particular cycle, the maximum (or maximum amplitude) corresponds to full inspiration in which the lungs are expanded or distended, and the minimum (or minimum amplitude) corresponds to full expiration in which the lungs are contracted or collapsed.

The signal characteristic processor 304 determines a mean (average) maximum 408 and a mean (average) minimum 410 respectively for the identified maxima $404_1$-$404_6$ and minima $406_1$-$406_6$.

The slope identifier 306 identifies descending (expiration or inspiration) and ascending (inspiration or expiration) regions or slopes and for each cycle based on the maxima $404_1$-$404_6$ and the minima $406_1$-$406_6$. For sake of clarity, only slopes 412 and 414 for the cycle $402_2$ are identified in FIG. 4 through reference numeral. Note that in FIG. 4, the rate of expiration (slope 412) is slower than the rate of inspiration (slope 414).

The phase-to-amplitude/slope mapper 308 maps motion phases respectively to the expiration and inspiration slopes 412 and 414, between the mean maximum 408 and the mean minimum 410. For example, the cycle $402_2$ spans from the maximum $404_2$ to the next maximum $404_3$, and the 0% phase is mapped to the mean maximum 408 and the 49% phase is mapped to the mean minimum 410.

Expiration, which occurs between the 0% and 49% phases of the cycle $402_2$, is mapped to the expiration slope 412, and inspiration, which occurs between 49% and 99% phases of the cycle $402_2$, is mapped to the inspiration slope 414. As such, the phases for expiration and inspiration are separately determined, which takes into consideration that the average rate of expiration is generally less than the average rate of inspiration. As such, each cycle is guaranteed to have data points corresponding to phases between 0% and 99%.

Some cycles may have more than one point that corresponds to a particular phase. In these cases, the first or other candidate point is selected. Where a cycle (e.g., the cycle $402_1$) includes a maximum that is less than the mean maximum (e.g., the maximum $404_1$), the cycle maximum is deemed 0%. Thus, in FIG. 4, the phase mapping would be suitably scaled to span from the maximum $404_1$ and the minimum $406_1$.

Figure 2:
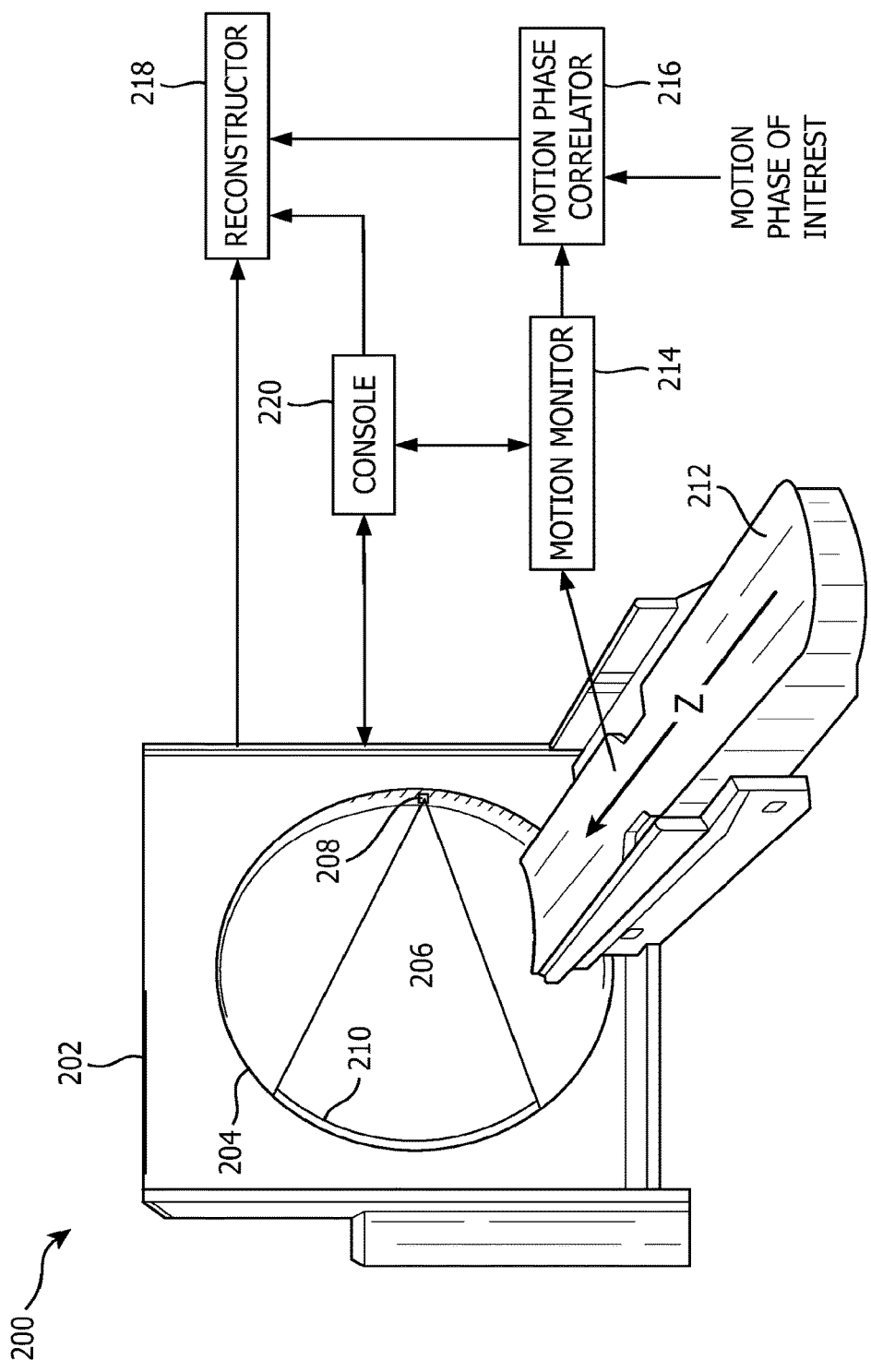
FIG. 2 illustrates an example imaging system in connection with a motion phase correlator.

The timestamp identifier 310 identifies imaging or scan acquisition timestamps for motion phases. For example, in FIG. 4, the timestamp identifier 310 is used to identify timestamps $416_1$-$416_6$ corresponding to the 25% phase of the motion cycles $402_1$-$402_6$. Of course timestamps corresponding to phases other than 25% can also be identified. The timestamp identifier 310 generates a signal indicative of the timestamps and conveys the signal to the reconstructor 218 (FIG. 2), which may select projection data to reconstruct based thereon.

As these timestamps correlate to substantially similar mechanical amplitude of the moving object, the structure of the moving object in the reconstructed image data will likely be well-aligned. This can be seen in FIGS. 5 and 6.

Figure 5:
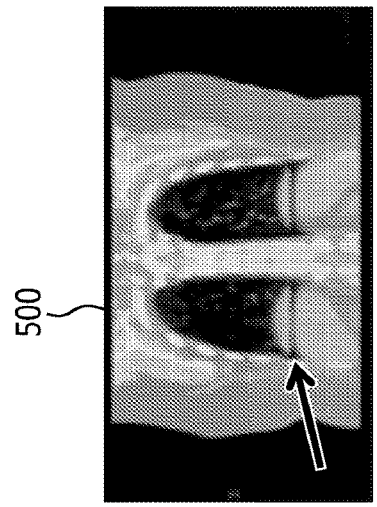
FIG. 5 illustrates an example image generated without use of the motion phase correlator.

FIG. 5 shows an image 500 reconstructed where such timestamps are not used to select the projection data to reconstruct, and the anatomical structure in the projection data is not aligned or misaligned, introducing artifact 502 into the image 500, as indicated by the arrow in the image. The artifact in FIG. 5 is provided for explanatory purposes, and other or different artifact may be present in the image.

Figure 6:
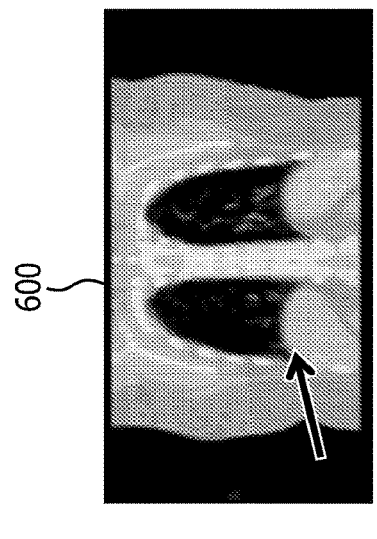
FIG. 6 illustrates an example image generated with projection data selected by the motion phase correlator.

FIG. 6 shows an image 600 reconstructed based on projection data corresponding to timestamps identified by the motion phase correlator 216 for a particular motion phase. Herein the anatomical structure in the projection data is aligned, and the artifact in image 500 is absent, as indicated by the arrow in the image.

Figure 7:
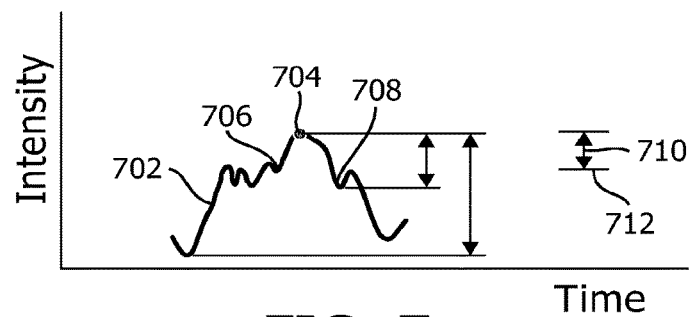
FIG. 7 illustrates example approach for identifying maxima in a motion signal.
Figure 8:
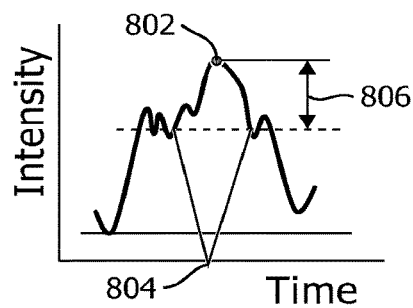
FIG. 8 illustrates example approach for identifying a local maximum amongst multiple maxima in a cycle.
Figure 9:
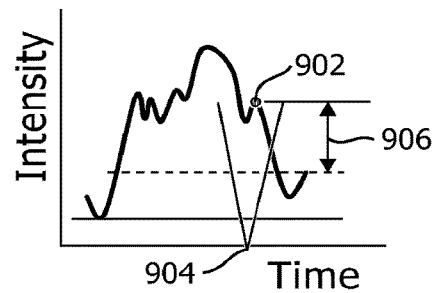
FIG. 9 illustrates example approach for rejecting maxima amongst multiple maxima candidates for a cycle.

As discussed above, the signal characteristic identifier 302 identifies one or more characteristics of a motion signal such as maxima and minima for cycles in a motion signal. It is to be appreciated that the motion signal may include noise, which may provide false maxima and/or minima in the signal and/or obscure true maxima and/or minima. FIGS. 7-9 illustrate an approach for determining the maxima and minima in the presence of noise. Examples of such signals include respiratory, cardiac, and/or other signals.

Initially referring to FIG. 7, a sub-portion of a noisy signal 702 is illustrated. Peaks or maxima are identified in the signal 702 for a predetermined evaluation range. In the illustrated example, a peak 704 is identified as the single highest point between two points 706 and 708, which are smaller by a predefined detection threshold 710. In this example, the threshold 710 is defined to be one tenth ($\frac{1}{10}$) of the signal's global dynamic range, or the difference between the global maximum and global minimum. In other embodiments, the threshold 710 can be otherwise defined.

Each data point of the signal 702 in the evaluation range is then evaluated. The data points of the signal 702 in the evaluation range before the data point 704 are searched until a data point drops below a second threshold 712, which corresponds to the amplitude from the minimum to the maximum less the threshold 710. Likewise, the data points of the signal 702 in the evaluation range after the data point 704 are searched until a data point drops below the second threshold 712. All of the data points in the evaluation range are then compared to the data point 704.

If the peak 704, over the evaluation range, is the maximum, it is identified as a local maximum. Otherwise, the search continues with the next point. This is further illustrated in FIGS. 8 and 9. In FIG. 8, a peak 802, identified in an evaluation range 804 based on a threshold 806, is identified as a local maximum as it is the highest point in the range 804. In FIG. 9, a peak 902 identified in an evaluation range 904, based on a threshold 906, is not identified as a local maximum as it is not the highest point in the range 904.

Figure 10:
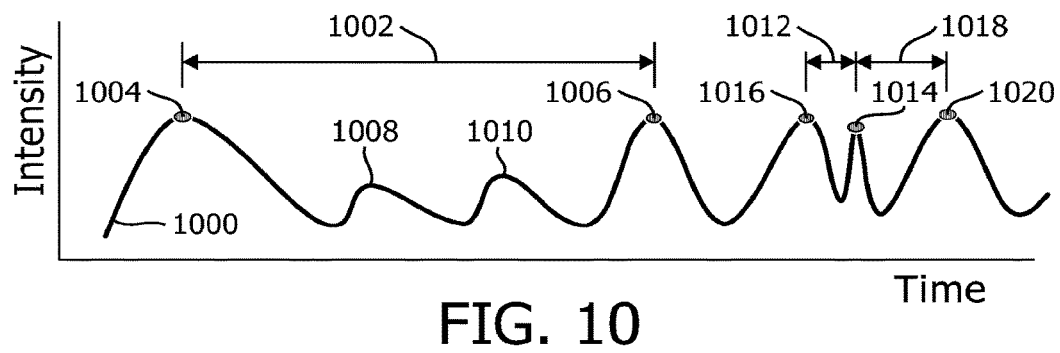
FIG. 10 illustrates example approach for augmenting a motion signal.

FIG. 10 illustrates a non-limiting technique for augmenting the signal.

With this technique, where a time distance 1002 between two peaks 1004 and 1006 of a motion signal 1000 exceeds an add peak threshold, one or more peak 1008 and 1010 are added to the signal 1000. Where the time distance 1012 between a peak 1014 and a preceding peak 1016 and a time distance 1018 between the maximum 1014 and a subsequent peak 1020 are both less than an extract peak threshold, the peak 1014 is removed from the signal 1000. The thresholds may be based on an average peak spacing or otherwise.

Figure 11:
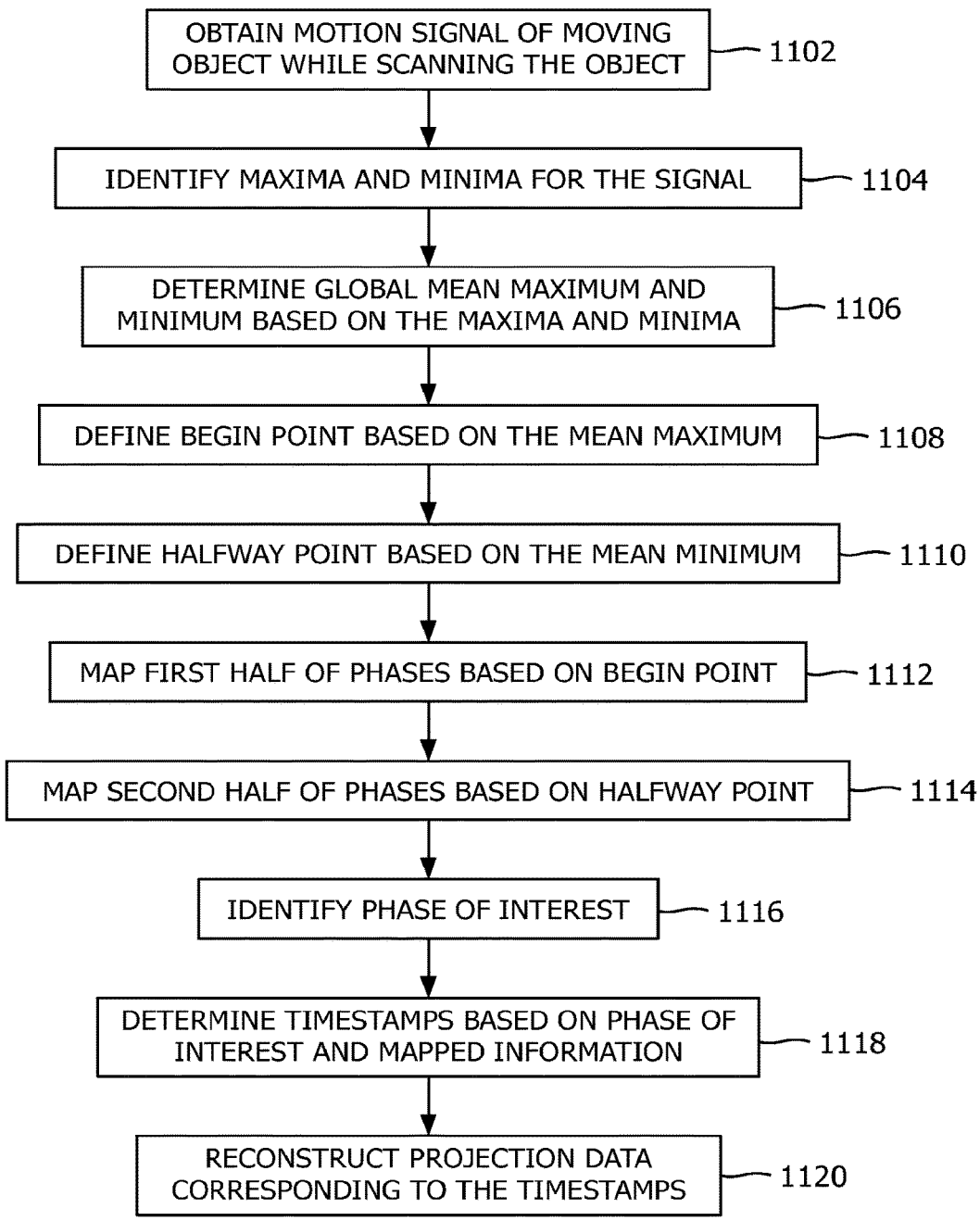
FIG. 11 illustrates an example method for identifying projection data for a motion phase of interest for reconstruction.

FIG. 11 illustrates a method for identifying projection data for a motion phase of interest for reconstruction.

At 1102, a motion signal is currently obtained whiled scanning a moving object have recurring cyclic motion. The motion may be related to breathing, the heart beating, or other cyclic motion.

At 1104, maxima and minima amplitudes are identified in the motion signal.

At 1106, a global mean maximum amplitude and a global mean minimum amplitude are determined based on the identified maxima and minima.

At 1108, the global mean maximum amplitude is used to define a begin or 0% point for a first region of each cycle extending from the cycle maximum to the cycle minimum. Where the global maximum is greater than the cycle maximum, the begin or 0% point is defined at the cycle maximum. Where the global maximum is less than the cycle maximum, the begin or 0% point is defined at the point following the cycle maximum whose amplitude best matches the global maximum.

At 1110, the global mean minimum amplitude is used to define the 50% point for a second region of each cycle extending from the cycle minimum to the maximum of the next cycle. Where the global mean minimum is less than the cycle minimum, the 50% point is defined at the cycle minimum. Where the global minimum is greater than the cycle minimum, the 50% point is defined at the point following the cycle minimum whose amplitude best matches the global minimum.

At 1112, motion phases from 0% to 49% are mapped to the first region.

At 1114, motion phases from 50% to 99% are mapped to the second region.

At 1116, a phase of interest is identified.

At 1118, the mapping between the identified phase and the amplitudes/slopes is used to determine a scan acquisition timestamp per cycle that corresponds to the mapped amplitude.

At 1120, projection data acquired at the identified timestamps is reconstructed into an image volume.

Figure 12:
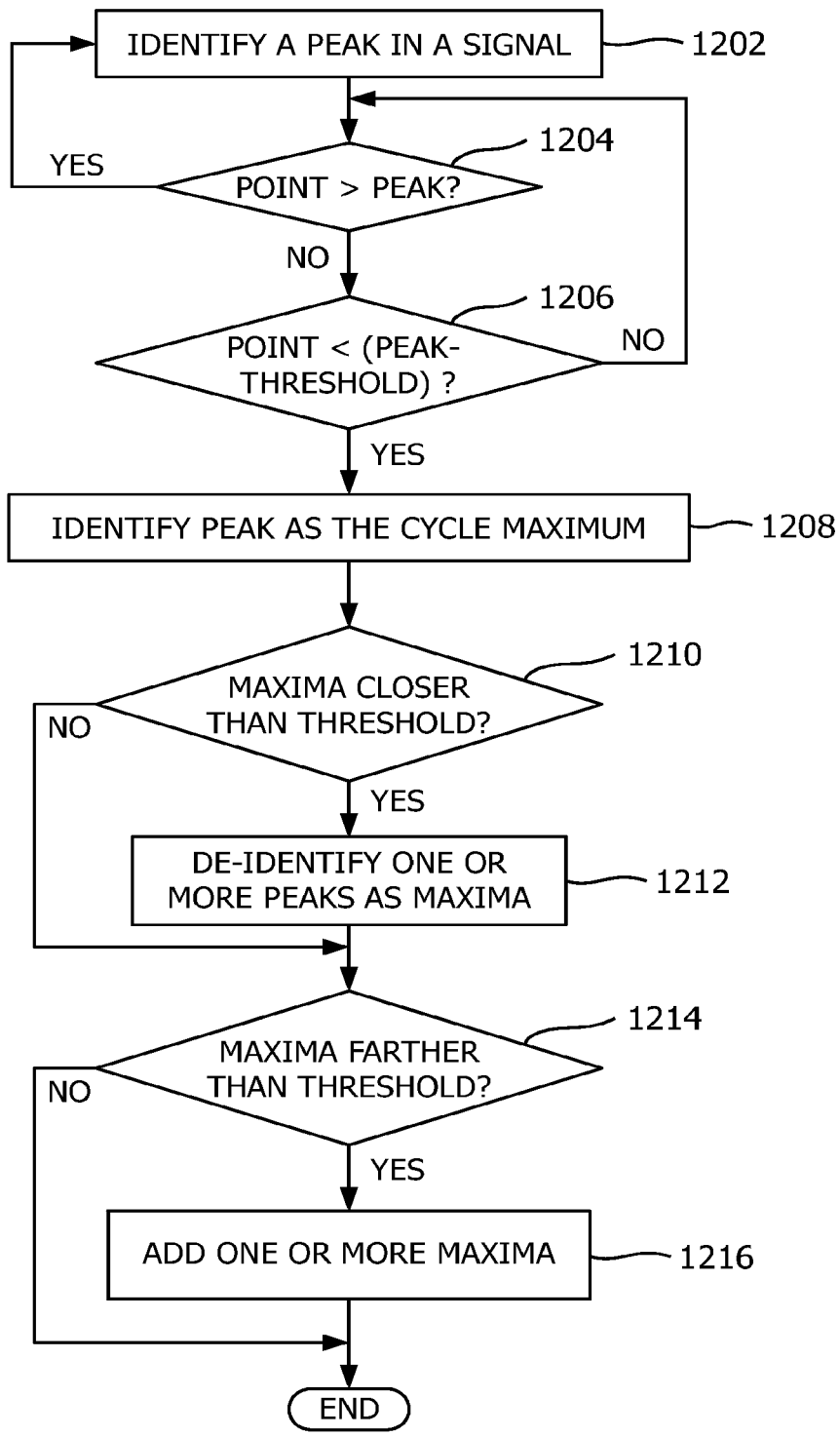
FIG. 12 illustrates an example method for determining the set of local maxima in a signal.

FIG. 12 illustrates a method for determining signal maximum.

At 1202, a peak is determined as the first point whose amplitude is greater than that of any previous point up to the previous cycle maximum by a predetermined threshold.

At 1204, it is determined whether a point following the peak exceeds the peak.

If so, then act 1202 is repeated with the next point.

If not, then at 1206, it is determined whether a point following the peak is less than the peak by a predetermined threshold.

If so, then at 1208 the peak is identified as a cycle maximum.

If not, then act 1204 is repeated with the next point.

At 1210, it is determined whether the maxima are closer together than a predetermined threshold.

If so, then at 1212, one or more of these maxima are de-identified (removed) as maxima. With one non-limiting embodiment, the mean and standard deviation of the spacing between maxima is calculated, and one or more of the maxima that are closer together than mean-x*standard deviation (where x is an input parameter) are de-identified as maxima.

If so, or if not, then 1214, it is determined whether the maxima are farther apart than a predetermined threshold.

If so, then at 1216, one or more of these maxima are added. With one non-limiting embodiment, the mean and standard deviation of the spacing between maxima is calculated, and if one or more of the maxima are farther apart than mean+x*standard deviation (where x in an input parameter) then one or more maxima are added between the bounding peaks, using acts 1202 through 1208, where the classification threshold is iteratively diminished until suitable maxima are identified.

The above described acts may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Although the above is discussed in the context of CT and respiratory signals, it is to be appreciated that the approach disclosed herein can be employed to identify substantially equivalent data points in another noisy cyclic signal with irregular periodicity.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system, comprising:
    a processor configured to:
    identify a set of motion signal timestamps, for a plurality of motion cycles in a continuous cyclical motion signal indicative of cyclic motion of a moving object, based on a predetermined motion phase of interest and a phase-to-amplitude/slope mapping, wherein the set of motion signal timestamps correspond to a common signal amplitude, wherein each descending amplitude region and each ascending amplitude region of the continuous cyclical motion signal is mapped using a lesser of a mean maximum and a local maximum, and a greater of a mean minimum and a local minimum, and divided for at least one of the local maximum less than the mean maximum or the local minimum greater than the mean minimum; and
    generate volumetric image data based on data acquired by a scanner and the identified set of motion signal timestamps.

2. The system of claim 1, further comprising:
    a signal characteristic identifier that identifies signal maxima and minima for one or more cycles of the motion signal; and
    a signal characteristic processor that determines the mean maximum and the mean minimum based on the identified maxima and minima.

3. The system of claim 2, wherein the signal characteristic identifier identifies a maximum for an evaluation range within a motion cycle as a point lying between two points with amplitudes below a maximum determining threshold, compares other points in the evaluation range before and after the maxima with the maximum; and identifies the maxima as a local maximum for the evaluation range when the maximum is greater than the compared other points.

4. The system of claim 2, further comprising:
    a signal slope identifier that identifies a descending amplitude region and an ascending amplitude region for each cycle; and
    a phase-to-amplitude/slope mapper that maps motion phases to the motion signal based on the mean maximum and the mean minimum and the descending and ascending amplitude regions.

5. The system of claim 4, further comprising:
    a timestamp identifier that identifies timestamps of the motion signal that correspond to predetermined phase of interest and a common signal amplitude.

6. The system of claim 5, wherein the timestamp identifier selects a phase based on a linearly divided amplitude in at least one of the ascending amplitude region or the descending amplitude region.

7. The system of claim 4, wherein the phase-to-amplitude/slope mapper maps motion phases the ascending amplitude regions separately from the descending amplitude regions.

8. The system of claim 4, wherein the phase-to-amplitude/slope mapper maps the motion phases dividing linearly each descending amplitude region and each ascending amplitude region between the mean maximum and the mean minimum by amplitude.

9. The system of claim 2, wherein the signal characteristic identifier removes at least one of the identified maxima based on a time distance between a preceding identified maxima and a subsequent local maxima less than an extract peak threshold.

10. A method, comprising:
    mapping phases to a descending region and an ascending region of a noisy continuous cyclic signal having irregular periodicity based on an identified local maximum which includes identifying each descending amplitude region and each ascending amplitude region using a lesser of a mean of local maximum and the local maximum, and a greater of a mean of local minimum and a local minimum, and dividing one of the descending region and the ascending region into phases for at least one local maximum less than the mean maximum or the local minimum greater than the mean minimum; and
    generating volumetric image data based on data acquired by a scanner and a selected motion phase from the mapped phases.

11. The method of claim 10, further comprising:
    correcting, after identifying a plurality of local maxima, a spacing between the plurality of local maxima.

12. The method of claim 11, wherein correcting includes removing at least one local maximum based on a time distance between a preceding local maximum and a subsequent local maximum that are less than a extract peak threshold.

13. The method of claim 10, further comprising:
    generating a map that maps motion phases to an amplitude of the noisy cyclic signal based on the peak and a slope of each motion cycle.

14. The method of claim 10, further comprising:
    identifying a set of motion signal timestamps for a plurality of motion cycles in the signal, wherein the timestamps are identified based on the map and correspond to predetermined phase of interest and a common signal amplitude.

* * * * *